(12) United States Patent
Guzman et al.

(10) Patent No.: US 9,757,209 B2
(45) Date of Patent: Sep. 12, 2017

(54) COMPOSITIONS AND METHODS FOR DENTAL APPLICATIONS INVOLVING ZINC-OXIDE CEMENTS

(71) Applicant: Essential Dental Systems, Inc., South Hackensack, NJ (US)

(72) Inventors: Jason Guzman, Union City, NJ (US); Jeffrey Wan, Westwood, NJ (US)

(73) Assignee: Essential Dental Systems, Inc., South Hackensack, NJ (US)

( * ) Notice: Subject to any disclaimer, the term of this patent is extended or adjusted under 35 U.S.C. 154(b) by 73 days.

(21) Appl. No.: 14/300,369

(22) Filed: Jun. 10, 2014

(65) Prior Publication Data

US 2015/0011452 A1 Jan. 8, 2015

Related U.S. Application Data

(60) Provisional application No. 61/842,487, filed on Jul. 3, 2013.

(51) Int. Cl.

| | |
|---|---|
| *A61C 5/02* | (2006.01) |
| *C11D 7/44* | (2006.01) |
| *A61K 6/00* | (2006.01) |
| *C11D 7/26* | (2006.01) |
| *C11D 7/32* | (2006.01) |
| *C11D 1/62* | (2006.01) |
| *C11D 3/20* | (2006.01) |
| *C11D 3/50* | (2006.01) |
| *A61K 6/083* | (2006.01) |
| *A61C 3/16* | (2006.01) |
| *A61C 5/40* | (2017.01) |

(52) U.S. Cl.
CPC ............ *A61C 5/02* (2013.01); *A61C 3/16* (2013.01); *A61C 5/40* (2017.02); *A61K 6/0023* (2013.01); *A61K 6/0047* (2013.01); *A61K 6/083* (2013.01); *C11D 1/62* (2013.01); *C11D 3/2093* (2013.01); *C11D 3/2096* (2013.01); *C11D 3/50* (2013.01); *C11D 7/266* (2013.01); *C11D 7/3209* (2013.01); *C11D 7/44* (2013.01)

(58) Field of Classification Search
CPC ...................................................... A61C 5/02

USPC .......................................................... 510/161
See application file for complete search history.

(56) References Cited

U.S. PATENT DOCUMENTS

| | | | |
|---|---|---|---|
| 5,311,632 A * | 5/1994 | Center ........................ | 15/22.1 |
| 5,662,888 A | 9/1997 | Diamond | |
| 6,626,673 B2 | 9/2003 | Abiru et al. | |
| 7,204,874 B2 * | 4/2007 | Jia et al. ..................... | 106/35 |
| 7,204,875 B2 * | 4/2007 | Jia et al. ..................... | 106/35 |
| 7,211,136 B2 * | 5/2007 | Jia et al. ..................... | 106/35 |
| 7,261,563 B2 | 8/2007 | Haschke | |
| 8,293,216 B2 | 10/2012 | Deckner et al. | |
| 8,962,026 B2 * | 2/2015 | Baker et al. ................. | 424/489 |
| 2002/0110787 A1 * | 8/2002 | Abiru et al. ................. | 433/224 |
| 2003/0152524 A1 * | 8/2003 | Eshita ..................... | A61K 8/29 |
| | | | 424/49 |
| 2005/0066854 A1 * | 3/2005 | Jia .............................. | 106/35 |
| 2006/0249705 A1 * | 11/2006 | Wang et al. ............. | 252/62.51 C |
| 2007/0053849 A1 * | 3/2007 | Doyle et al. ................ | 424/50 |
| 2008/0221003 A1 * | 9/2008 | Meine et al. ................ | 510/103 |
| 2009/0099075 A1 * | 4/2009 | Barg et al. .................. | 514/12 |
| 2009/0156485 A1 * | 6/2009 | Barg et al. .................. | 514/12 |
| 2010/0136069 A1 | 6/2010 | Deckner et al. | |
| 2011/0046262 A1 * | 2/2011 | Bublewitz ............. | A61K 6/0008 |
| | | | 523/121 |
| 2015/0011452 A1 * | 1/2015 | Guzman et al. ............ | 510/161 |

FOREIGN PATENT DOCUMENTS

EP 0674896 a1 * 10/1994

* cited by examiner

*Primary Examiner* — Nicole M Buie-Hatcher
*Assistant Examiner* — M. Reza Asdjodi
(74) *Attorney, Agent, or Firm* — Lerner, David, Littenberg, Krumholz & Mentlik, LLP (57) ABSTRACT

Described are compositions and methods for the removal of zinc-oxide eugenol-based temporary cements or root canal filling materials from a variety of surfaces including surfaces inside the oral cavity, such as teeth, as well as surfaces of objects located outside of the oral cavity, such as instruments and prostheses. In certain compositions, the resin-dentin bond between permanent cements and collagen-containing surfaces can be increased. The compositions are non-toxic, can be used inside the oral cavity, and do not require special disposal procedures.

8 Claims, 6 Drawing Sheets

COMPOSITIONS AND METHODS FOR DENTAL APPLICATIONS INVOLVING ZINC-OXIDE CEMENTS

CROSS-REFERENCE TO RELATED APPLICATIONS

The present application claims the benefit of the filing date of U.S. Provisional Patent Application No. 61/842,487, filed Jul. 3, 2013, the disclosure of which is hereby incorporated herein by reference.

BACKGROUND OF THE INVENTION

Temporary dental cements are routinely used for the temporary cementation of crowns and other prostheses to dentin and enamel surfaces. Many of the commonly used temporary dental cements contain zinc-oxide eugenol (ZOE) due to its short setting time and good short-term marginal sealing effects. After a tooth restoration procedure has been performed using ZOE-containing cements, instruments and work-pieces must be cleaned in order to remove these cements. These ZOE-containing temporary cements must also be thoroughly removed from collagen-containing surfaces, such as dentin, enamel and bone, during tooth restorations as well as from temporary crowns and other prostheses before applying a resin-based permanent cement. Permanent prostheses are often cemented with acrylate resin-based compositions. The bonding ability of these permanent resin cements is severely hindered by the presence of eugenol in the temporary cement, undermining the success of the permanent restorations. This is due to the fact that eugenol is a problematic inhibitor of polymerization of composite restorative polymeric materials in permanent cements.

Current methods for removing temporary cement from instruments, work-pieces, prostheses, and collagen-containing surfaces are inadequate, as gross amounts of cement remain on the surface. This may result in unintended contamination of the residual cement with other chemicals when the instrument is subsequently used for another procedure. In addition, current ZOE-removing compositions are toxic, rendering them incapable of internal use in the oral cavity and requiring special disposal procedures. For example, currently available temporary cement removers, such as Advanced Formula Temporary Cement Remover (L&R Manufacturing Company) and VK-6 Temporary Cement Remover (Heraeus Kulzer North America), contain harsh inorganic bases, and therefore, can only be used outside the oral cavity. Currently, there is no commercially available temporary cement removal that is safe for use inside the oral cavity.

Accordingly, there is a need for compositions that effectively and efficiently remove ZOE-based temporary cements from a variety of surfaces. In addition, these compositions must be non-toxic so that they can be used on collagen-containing surfaces within the oral cavity and so as not to require special disposal procedures.

During tooth restoration procedures, temporary cements are removed and replaced with permanent cements, such as cements containing acrylate resins. Therefore, efforts have been made to not only thoroughly remove the temporary cements from the tooth, but to increase the adhesion of the acrylate resin permanent cements to collagen-containing surfaces such as the dentin of the tooth. The acrylate resin-dentin bond between permanent cements and collagen-containing surfaces can be strengthened with the use of desensitizing agents. Accordingly, there is a need for a single composition that effectively and efficiently removes ZOE-based temporary cements from a variety of surfaces as well as strengthens the resin-dentin bond between permanent cements and collagen-containing surfaces.

Treatment of pulp disease or apical periodontitis commonly involves the insertion of a gutta-percha cone into the root canal, followed by the sealing of the canal with a dental cement. Dental gutta-percha cones and sealants are typically composed of ZOE. However, the use of ZOE does not always provide a long-lasting seal, resulting in possible bacterial infiltration and infection. In such cases, it is necessary to re-treat the canal. Current methods of re-treating include removal of the gutta-percha cone and cement sealer via mechanical instrumentation with a reamer or file Because the gutta-percha cone and sealer materials are tough, using a reamer or file is often time consuming and inadequate. A practitioner may often use toxic chemicals, such as chloroform and xylene, to aid in the removal of the root canal materials; however, these chemicals must be used in very small quantities as they are known carcinogens. Accordingly, there is a need for a non-toxic composition for removing root canal filling materials during endodontic re-treatment cases.

BRIEF SUMMARY OF THE INVENTION

The compositions and methods described herein allow for the effective removal of ZOE-based temporary cements or root canal filling materials from a variety of surfaces including surfaces inside the oral cavity, such as teeth, as well as surfaces of objects located outside of the oral cavity, such as instruments and prostheses. In certain embodiments, the compositions can also strengthen the resin-dentin bond between permanent cements and collagen-containing surfaces. Importantly, all of the compositions described herein are non-toxic, can be used inside the oral cavity, and do not require special disposal procedures.

One aspect described herein includes compositions and methods for removing zinc-oxide eugenol (ZOE)-containing temporary cements from living and non-living objects. These compositions and methods comprise at least one essential oil, at least one aliphatic ester, at least one cyclic ester, and at least one quaternary ammonium salt. Methods for removing ZOE-containing cements involve chemically dissolving the ZOE from the surface of the object by immersing or coating the object with the composition containing at least one essential oil, at least one aliphatic ester, at least one cyclic ester, and at least one quaternary ammonium salt. After chemical dissolution, mechanical treatment can optionally be performed in order to aid in removal of any residual ZOE from the surface of the object.

In one embodiment, described herein is an orally-acceptable composition for removing zinc-oxide eugenol (ZOE)-containing temporary cements comprising at least one essential oil, at least one aliphatic ester, at least one cyclic ester, and at least one quaternary ammonium salt.

In one embodiment, described herein is an orally-acceptable composition for removing zinc-oxide eugenol (ZOE)-containing temporary cements consisting of at least one essential oil, at least one aliphatic ester, at least one cyclic ester, and at least one quaternary ammonium salt.

Another aspect described herein includes compositions and methods for providing or promoting bonding between a collagen-containing surface and an acrylate resin. These compositions comprise at least one essential oil, at least one aliphatic ester, at least one cyclic ester, at least one desensitizer, at least one quaternary ammonium salt, at least one alcohol, and, optionally, at least one preservative. Methods for providing or promoting bonding between a collagen-containing surface and an acrylate resin include applying a volume of the composition comprising at least one essential oil, at least one aliphatic ester, at least one cyclic ester, at least one desensitizer, at least one quaternary ammonium salt, at least one alcohol, and, optionally, at least one preservative. After applying the composition, mechanical treatment can optionally be performed in order to aid in removal of any residual ZOE from the surface as well as increase adhesion between the collagen-containing surface and acrylate resin.

In one embodiment, described herein is an orally-acceptable composition for removing zinc-oxide eugenol (ZOE)-containing temporary cements as well as providing or promoting bonding between a collagen-containing surface and an acrylate resin comprising at least one essential oil, at least one aliphatic ester, at least one cyclic ester, at least one desensitizer, at least one quaternary ammonium salt, at least one alcohol, and, optionally, at least one preservative.

In one embodiment, described herein is an orally-acceptable composition for removing zinc-oxide eugenol (ZOE)-containing temporary cements as well as providing or promoting bonding between a collagen-containing surface and an acrylate resin consisting of at least one essential oil, at least one aliphatic ester, at least one cyclic ester, at least one desensitizer, at least one quaternary ammonium salt, at least one alcohol, and, optionally, at least one preservative.

Yet another aspect described herein includes compositions and methods for removing root canal filling materials. These compositions comprise at least one essential oil, at least one aliphatic ester, optionally at least one cyclic ester, and optionally at least one quaternary ammonium salt. Methods for removing root canal filling materials include chemically dissolving the root canal filling material by applying a volume of the composition comprising at least one essential oil, at least one aliphatic ester, optionally at least one cyclic ester, and optionally at least one quaternary ammonium salt to the root canal filling material. After chemical dissolution, mechanical treatment can optionally be performed in order to aid in removal of any residual root canal filling materials from the surface of the tooth.

In one embodiment, the compositions and methods for removing root canal filling materials consist of at least one essential oil, at least one aliphatic ester, optionally at least one cyclic ester, and optionally at least one quaternary ammonium salt.

DETAILED DESCRIPTION

Removing ZOE-Containing Cements

Described herein are compositions and methods for removing zinc-oxide eugenol (ZOE)-containing temporary cements from living objects inside the oral cavity, i.e., from collagen-containing surfaces such as teeth, as well as from non-living objects, such as prostheses and dental instruments. The compositions can efficiently and effectively remove ZOE-containing temporary cements from said surfaces and are safe for use inside the oral cavity. In one embodiment, a composition for removing zinc-oxide eugenol-based products from a living or non-living object comprises at least one essential oil, at least one aliphatic ester, at least one cyclic ester, and at least one quaternary ammonium salt.

Essential oils are known to those skilled in the art and are not described in detail herein. Essential oils are non-toxic non-polar compounds that aid in the dissolution of the temporary cement. In one embodiment the essential oil is at least one of limonene, eucalyptol, and ethyl heptanoate. In another embodiment, the total concentration of essential oils is about 50% to about 99% parts by weight of the total composition.

Aliphatic esters are known to those skilled in the art and are not described in detail herein. Aliphatic esters are non-toxic polar compounds that aid in the dissolution of the temporary cement as well as provide a pleasing odor to the composition. In one embodiment the aliphatic ester is at least one of isopentyl acetate, isoamyl acetate, isobutyl acetate, benzyl acetate, methyl salicylate, ethyl acetate, and propyl acetate. In another embodiment, the total concentration of aliphatic esters is about 5% to about 40% parts by weight of the total composition.

Cyclic esters are known to those skilled in the art and are not described in detail herein. Cyclic esters are nontoxic and aid in treating collagen-containing surfaces for subsequent cementation. In one embodiment the cyclic ester is at least one of propylene carbonate and propiolactone. In another embodiment, the total concentration of cyclic esters is about 0.1% to about 6% parts by weight of the total composition.

Quaternary ammonium salts are known to those skilled in the art and are not described in detail herein. Quaternary ammonium salts are non-toxic and act as a detergent by cleaning the surface of dissolved cement or other debris. In one embodiment, the quaternary ammonium salt is at least one of tetra-n-butylammonium bromide, cetrimonium bromide, and benzalkonium chloride. In another embodiment, the total concentration of quaternary ammonium salts is about 0.01% to about 4% parts by weight of the total composition.

In one embodiment, the compositions comprises about 70% to about 90% parts by weight of the total composition of at least one essential oil; about 10% to about 30% parts by weight of the total composition of at least one aliphatic ester; about 1% to about 5% parts by weight of the total composition of at least one cyclic ester; and about 0.05% to about 2% parts by weight of the total composition of the at least one quaternary ammonium salt.

In another embodiment the composition comprises about 80% parts by weight of the total composition of limonene; about 10% parts by weight of the total composition of isopentyl acetate; about 6.9% parts by weight of the total composition of isobutyl acetate; about 3% parts by weight of the total composition of propylene carbonate; and about 0.1% parts by weight of the total composition of benzalkonium chloride.

In one embodiment, described herein is an orally-acceptable composition for removing zinc-oxide eugenol (ZOE)-containing temporary cements comprising at least one essential oil, at least one aliphatic ester, at least one cyclic ester, and at least one quaternary ammonium salt.

The compositions described herein aid in the removal of ZOE-containing temporary cements from both living and non-living surfaces. Living surfaces may include collagen-containing surfaces found inside the oral cavity. In one embodiment the living surface includes dentin, enamel, and bone. Non-living surfaces may include dental instruments as well as work-pieces such as bridges, crowns, inlays, onlays, and prostheses.

One aspect described herein includes methods for removing ZOE-based temporary cements from various objects. These methods involve chemically dissolving the ZOE from the surface of the object by immersing or coating the object with any of the compositions described herein comprising at least one essential oil, at least one aliphatic ester, at least one cyclic ester, and at least one quaternary ammonium salt. After chemical dissolution, mechanical treatment can optionally be performed in order to aid in removal of any residual ZOE from the surface of the object. These methods can be performed a single time or can be repeated as necessary in order to maximize removal of ZOE-containing cements from the object.

The volume of composition required to chemically dissolve the ZOE from the object is not limited so long as the volume is sufficient to coat or immerse the object with the composition. For living objects located inside the oral cavity, such as teeth, smaller volumes, e.g., about 0.1 ml, may be sufficient to coat the object. In one embodiment, the volume of composition used to coat a tooth located inside the oral cavity is in the range of about 0.1 ml to about 1 ml. For larger objects located outside of the oral cavity, such as prosthesis or dental instruments, larger volumes, e.g., about 10 ml, may be needed to coat the object, particularly if the object is to be completely immersed by the composition. In one embodiment, the volume of composition used to coat or immerse an object located outside the oral cavity is in the range of about 1 ml to about 1 liter.

The length of time of chemical dissolution is not limited so long as the time is sufficient to dissolve the ZOE from the object. In one embodiment, the object is immersed or coated with the composition for up to about ten minutes. In another embodiment, the object is immersed or coating with the composition for up to about five minutes.

After chemical dissolution, the object may optionally be subjected to mechanical treatment to aid in removal of any residual ZOE from the surface of the object that was not completely removed by chemical dissolution. For objects located inside the oral cavity, mechanical treatment may include scraping, rubbing, brushing, or combinations thereof. For objects located outside of the oral cavity, mechanical treatment may include subjecting the object to vibrations, ultrasound, or combinations thereof.

In one embodiment, the method for removing ZOE-based temporary cements from an object comprises chemically dissolving the ZOE from the surface of the object by immersing or coating the object with a composition comprising about 80% by weight of the total composition of limonene; about 10% by weight of the total composition of isopentyl acetate; about 6.9% parts by weight of the total composition of isobutyl acetate; about 3% parts by weight of the total composition of propyl carbonate; and about 0.1% parts by weight of the total composition of benzalkonium chloride. After chemical dissolution, mechanical treatment can optionally be performed in order to aid in removal of any residual ZOE from the surface of the object.

In one embodiment, the methods include chemically dissolving the ZOE from the surface of an object by immersing or coating the object with an orally-acceptable composition comprising at least one essential oil, at least one aliphatic ester, at least one cyclic ester, and at least one quaternary ammonium salt. After chemical dissolution, mechanical treatment can optionally be performed in order to aid in removal of any residual ZOE from the surface of the object. These methods can be performed a single time or can be repeated as necessary in order to maximize removal of ZOE-containing cements from the object.

Promotion of Resin-Collagen Adhesion

ZOE-containing temporary cements must be thoroughly removed from collagen-containing surfaces, such as dentin, enamel and bone, during tooth restorations as well as from temporary crowns and other prostheses before applying an acrylate resin-based permanent cement. Applicants have discovered that by adding a desensitizing agent, such as shellac, to the compositions for removing ZOE-containing cements, not only is the temporary cement containing eugenol efficiently removed, but adhesion of the resin-based permanent cement to the collagen surface is increased.

In one embodiment, a composition for providing bonding between a collagen-containing surface and an acrylate resin cement comprises at least one essential oil, at least one aliphatic ester, at least one cyclic ester, at least one quaternary ammonium salt, at least one desensitizer, and at least one alcohol. The compositions can optionally include at least one additive, such as a preservative. As with the compositions for removing ZOE-containing cements, the compositions described herein for promoting resin-collagen adhesion are non-toxic, can be used inside the oral cavity, and do not require special disposal procedures.

The choice of desensitizing agent is not limited so long as the agent is capable of increasing or promoting adhesion of the resin to collagen-containing surfaces. Without being bound by a particular theory, it is believed that the compositions described herein which contain a desensitizing agent increase adhesion of the acrylate resin cement to the collagen surface by occluding the dentinal tubules, providing a smoother surface for resin bonding. One exemplary desensitizing agent discovered by the Applicant is shellac. Shellac is a natural, non-toxic polymer and therefore, is safe for use in the oral cavity. Additional exemplary desensitizers may include hydroxyethyl methacrylate and glutaraldehyde. In one embodiment, the total concentration of desensitizer is about 0.5% to about 50% parts by weight of the total composition. In another embodiment, the desensitizer is shellac used at a concentration of about 0.5% to about 10% parts by weight of the total composition. In yet another embodiment, the desensitizer is hydroxyethyl methacrylate and/or glutaraldehyde used at a concentration of about 25% to about 45% parts by weight of the total composition.

Alcohols are known to those skilled in the art and are not described in detail herein. Alcohols help stabilize the formulation, particularly when certain desensitizers are used. For example, if shellac is used as the desensitizer, the addition of alcohol helps to keep the shellac in solution. In one embodiment the alcohol is at least one of ethanol, benzyl alcohol, and isopropyl alcohol. In another embodiment, the total concentration of alcohol is about 5% to about 99% parts by weight of the total composition.

Preservatives are known to those skilled in the art and are not described in detail herein. Preservatives help stabilize the formulation, particularly when certain desensitizers are used. For example, if hydroxyethyl methacrylate is used as the desensitizer, the addition of a preservative helps to keep the hydroxyethyl methacrylate in solution. In one embodiment the preservative is at least one of butylated hydroxytoluene and tertiary butylhydroquinone. In another embodiment, the total concentration of preservative is about 0.001% to about 0.3% weight parts by weight of the total composition.

The choice of essential oil(s), aliphatic ester(s), cyclic ester(s), and quaternary ammonium salt(s) is not limited as discussed above. The amount of essential oil(s), aliphatic ester(s), cyclic ester(s), and quaternary ammonium salt(s) is optimized in order to allow for the additional constituents in the composition that provide bonding between the collagen-containing surface and the acrylate resin cement, i.e., desensitizer, alcohol, and preservative. In one embodiment, in addition to the above ranges as to the desensitizer, alcohol, and preservative, the total concentration of essential oils is about 1% to about 40% parts by weight of the total composition; the total concentration of aliphatic esters is about 0.1% to about 10% parts by weight of the total composition; the total concentration of cyclic esters is about 0.05% to about 5% parts by weight of the total composition; and the total concentration of quaternary ammonium salts is about 0.05% to about 1% parts by weight of the total composition.

In another embodiment, the composition comprises about 2.5% to about 30% parts by weight of the total composition of at least one essential oil; about 0.75% to about 5% parts by weight of the total composition of at least one aliphatic ester; about 0.1% to about 2% parts by weight of the total composition of at least one cyclic ester; about 0.05% to about 1% parts by weight of the total composition of at least one quaternary ammonium salt; about 0.5% to about 50% parts by weight of the total composition of the at least one desensitizer; about 20% to about 99% parts by weight of the total composition of at least one alcohol; and about 0.005% to about 0.05% parts by weight of the total composition of at least one preservative.

In another embodiment, the composition comprises about 3% to about 25% parts by weight of the total composition of at least one essential oil; about 0.8% to about 4.5% parts by weight of the total composition of at least one aliphatic ester; about 0.1% to about 1% parts by weight of the total composition of at least one cyclic ester; about 0.05% to about 0.5% parts by weight of the total composition of at least one quaternary ammonium salt; about 0.5% to about 10% parts by weight of the total composition of shellac or about 25% to about 45% parts by weight of the total composition of hydroxyethyl methacrylate; about 30% to about 95% parts by weight of the total composition of at least one alcohol; and about 0.075% to about 0.25% parts by weight of the total composition of at least one preservative.

In yet another embodiment, the composition comprises about 4% to about 20% parts by weight of the total composition of limonene; about 0.5% to about 3% parts by weight of the total composition of isopentyl acetate; about 0.3% to about 2% parts by weight of the total composition of isobutyl acetate; about 0.1% to about 1% parts by weight of the total composition of propylene carbonate; about 0.1% parts by weight of the total composition of benzalkonium chloride; about 5% parts by weight of the total composition of shellac; about 60% to about 90% parts by weight of the total composition of ethanol; and about 0.01% parts by weight of the total composition of butylated hydroxytoluene.

In still yet another embodiment, the composition comprises about 4% to about 20% parts by weight of the total composition of limonene; about 0.5% to about 3% parts by weight of the total composition of isopentyl acetate; about 0.3% to about 2% parts by weight of the total composition of isobutyl acetate; about 0.1% to about 1% parts by weight of the total composition of propylene carbonate; about 0.1% parts by weight of the total composition of benzalkonium chloride; about 35% parts by weight of the total composition of hydroxyethyl methacrylate; about 30% to about 60% parts by weight of the total composition of ethanol; and about 0.01% parts by weight of the total composition of butylated hydroxytoluene.

In one embodiment, described herein is an orally-acceptable composition for removing zinc-oxide eugenol (ZOE)-containing temporary cements as well as providing or promoting bonding between a collagen-containing surface and an acrylate resin comprising at least one essential oil, at least one aliphatic ester, at least one cyclic ester, at least one desensitizer, at least one quaternary ammonium salt, at least one alcohol, and, optionally, at least one preservative.

One aspect described herein includes methods for increasing bonding between collagen-containing surfaces, such as dentin, enamel and bone, with acrylate resin cements. These methods involve applying a volume of the composition described herein containing a desensitizer to a collagen-containing surface. In one embodiment, the composition comprises at least one essential oil, at least one aliphatic ester, at least one cyclic ester, at least one quaternary ammonium salt, at least one desensitizer, at least one alcohol, and, optionally, at least one preservative. After applying the composition, mechanical treatment can optionally be performed in order to aid in removal of any residual ZOE from the surface as well as increase adhesion between the collagen-containing surface and acrylate resin cement. The surface is then blasted with air for a period of time before applying the acrylate resin cement. These methods can be performed a single time or can be repeated as necessary in order to maximize removal of ZOE-containing cements from the surface as well as increase adhesion of the resin cement.

The volume of composition required to chemically dissolve the ZOE from the surface and increase adhesion is not limited so long as the volume is sufficient to coat the surface of the object with the composition. Collagen-containing surfaces are generally living objects located inside the oral cavity, and as such, would require smaller volumes, e.g., 0.1 ml, to sufficiently coat the surface. In one embodiment, the volume of composition used to coat a tooth located inside the oral cavity is in the range of about 0.1 ml to about 1 ml.

The length of time for applying the composition to the collagen-containing surface is not limited so long as the time is sufficient to dissolve any residual ZOE from the surface as well as increase adhesion of the resin. In one embodiment, the surface is coated with the composition for up to about 5 minutes. In another embodiment, the surface is coated with the composition for up to about 1 minute. In yet another embodiment, the surface is coated with the composition for up to 30 seconds.

After coating the surface, the surface may optionally be subjected to mechanical treatment to aid in removal of any residual composition or ZOE from the surface of the object prior to applying the acrylate resin cement. Mechanical treatment may include scraping, rubbing, brushing, or combinations thereof.

In one embodiment, after coating the surface or after optional mechanical treatment, the surface is then blasted with air for a period of time, for example, for about 10 seconds to about 15 seconds. This allows for a clean, dry surface prior to applying the acrylate resin cement to the collagen-containing surface.

In one embodiment, the method for increasing bonding between collagen-containing surfaces and acrylate resins comprises coating the surface of the object with a composition comprising about 4% to about 20% parts by weight of the total composition of limonene; about 0.5% to about 3% parts by weight of the total composition of isopentyl acetate; about 0.3% to about 2% parts by weight of the total composition of isobutyl acetate; about 0.1% to about 1% parts by weight of the total composition of propylene carbonate; about 0.1% parts by weight of the total composition of benzalkonium chloride; about 5% parts by weight of the total composition of shellac; about 60% to about 90% parts by weight of the total composition of ethanol; and about 0.01% parts by weight of the total composition of butylated hydroxytoluene. After coating the collagen-containing surface, mechanical treatment can optionally be performed in order to aid in removal of any residual composition or ZOE-containing cement from the surface of the object.

In another embodiment, the method for increasing bonding between collagen-containing surfaces and acrylate resins comprises coating the surface of the object with a composition comprising about 4% to about 20% parts by weight of the total composition of limonene; about 0.5% to about 3% parts by weight of the total composition of isopentyl acetate; about 0.3% to about 2% parts by weight of the total composition of isobutyl acetate; about 0.1% to about 1% parts by weight of the total composition of propylene carbonate; about 0.1% parts by weight of the total composition of benzalkonium chloride; about 35% parts by weight of the total composition of hydroxyethyl methacrylate; about 30% to about 60% parts by weight of the total composition of ethanol; and about 0.01% parts by weight of the total composition of butylated hydroxytoluene. After coating the collagen-containing surface, mechanical treatment can optionally be performed in order to aid in removal of any residual composition or ZOE-containing cement from the surface of the object.

In one embodiment, described herein is a method for removing zinc-oxide eugenol (ZOE)-containing temporary cements as well as providing or promoting bonding between a collagen-containing surface and an acrylate resin comprising applying a volume of an orally-acceptable composition comprising at least one essential oil, at least one aliphatic ester, at least one cyclic ester, at least one quaternary ammonium salt, at least one desensitizer, at least one alcohol, and, optionally, at least one preservative. After applying the orally-acceptable composition, mechanical treatment can optionally be performed in order to aid in removal of any residual ZOE from the surface as well as increase adhesion between the collagen-containing surface and acrylate resin cement.

Removal of Root Canal Fillings

Current procedures for re-treatment of root canal filling materials involve removal of the gutta-percha cone and cement sealer via mechanical instrumentation such as a reamer or file. These mechanical methods are often insufficient to remove all of the materials and may require the use of toxic chemicals to aid the complete dissolution and removal of the root canal filling materials. The compositions and methods described herein allow for gentle chemical dissolution of root canal filling materials from a tooth, such as a gutta-percha cone and sealer, without the need for harsh mechanical means of removal.

In one embodiment, the compositions contain at least one essential oil, at least one aliphatic ester, optionally at least one cyclic ester, and optionally, at least one quaternary ammonium salt. As with the compositions described herein for removing ZOE-containing cements and increasing adhesion of acrylate resins, the compositions for removing root canal filling materials are non-toxic, can be used inside the oral cavity, and do not require special disposal procedures. In another embodiment, the composition does not contain a surfactant.

Essential oils are known to those skilled in the art and are not described in detail herein. Essential oils are non-toxic non-polar compounds that aid in the dissolution of the root canal filling materials. In one embodiment the essential oil is at least one of limonene, eucalyptol, and ethyl heptanoate. In another embodiment, the total concentration of essential oils is about 60% to about 99% parts by weight of the total composition.

Aliphatic esters are known to those skilled in the art and are not described in detail herein. Aliphatic esters are non-toxic polar compounds that aid in the dissolution of the root canal filling materials as well as provide a pleasing odor to the composition. In one embodiment the aliphatic ester is at least one of isopentyl acetate, isoamyl acetate isobutyl acetate, benzyl acetate, methyl salicylate, ethyl acetate, and propyl acetate. In another embodiment, the total concentration of aliphatic esters is about 1% to about 30% parts by weight of the total composition.

Cyclic esters are known to those skilled in the art and are not described in detail herein. Cyclic esters are nontoxic and aid in treating the tooth for subsequent re-treatment. In one embodiment the cyclic ester is at least one of propylene carbonate and propiolactone. In another embodiment, the total concentration of cyclic esters is about 0.1% to about 10% parts by weight of the total composition.

Quaternary ammonium salts are known to those skilled in the art and are not described in detail herein. Quaternary ammonium salts are non-toxic and act as a detergent by cleaning the surface of dissolved materials and other debris. In one embodiment, the quaternary ammonium salt, if present, is at least one of tetra-n-butylammonium bromide, cetrimonium bromide, and benzalkonium chloride. In another embodiment, the total concentration of quaternary ammonium salts, if present, is about 0.01% to about 10% parts by weight of the total composition.

In one embodiment, the composition comprises about 85% to about 95% parts by weight of the total composition of at least one essential oil; and about 5% to about 20% parts by weight of the total composition of at least one aliphatic ester.

In another embodiment the composition comprises about 80% by weight of the total composition of limonene; about 10% by weight of the total composition of ethyl heptanoate; and about 10% parts by weight of the total composition of propyl acetate.

One aspect described herein includes methods for removing root canal filling materials, such as a gutta-percha cone and sealer, during a re-treatment procedure. These methods involve applying a volume of the composition described herein containing at least one essential oil and at least one aliphatic ester in order to chemically dissolve the root canal filling materials. After chemical dissolution, mechanical treatment can optionally be performed in order to aid in removal of any residual root canal filling materials from the tooth. These methods can be performed a single time or can be repeated as necessary in order to maximize removal of the root canal filling materials.

The volume of composition required to apply to the tooth is not limited so long as the volume is sufficient to coat the surface of the tooth, specifically, the root canal filling materials, with the composition. In one embodiment, the volume of composition used to coat a tooth containing root canal filling materials is in the range of about 0.1 ml to about 1 ml.

The length of time for applying the composition to the root canal filling material is not limited so long as the time is sufficient to chemically dissolve the root canal filling materials, including gutta-percha cone and sealer. In one embodiment, the tooth is coated with the composition for up to about ten minutes. In another embodiment, the tooth is coated with the composition for up to about three minutes.

After dissolution of the root canal materials, the tooth may optionally be subjected to mechanical treatment to aid in removal of any residual root canal materials from the tooth and oral cavity. Mechanical treatment may include scraping, rubbing, brushing, or combinations thereof. In another embodiment, the mechanical treatment does not include harsh mechanical treatment such as reaming and filing.

In one embodiment, the method for removing root canal filling materials during a re-treatment procedure comprises coating the tooth with a composition comprising about 80% parts by weight of the total composition of limonene; about 10% parts by weight of the total composition of ethyl heptanoate; and about 10% parts by weight of the total composition of propyl acetate to dissolve the root canal filling materials. After chemical dissolution, mechanical treatment can optionally be performed in order to aid in removal of any residual root canal filling materials from the tooth and oral cavity.

In another embodiment, the method for removing root canal filling materials during a re-treatment procedure comprises coating the tooth with a composition comprising about 80% parts by weight of the total composition of limonene; about 10% parts by weight of the total composition of ethyl heptanoate; and about 10% parts by weight of the total composition of propyl acetate to dissolve the root canal filling materials. In this embodiment, the composition does not contain a surfactant. After chemical dissolution, mechanical treatment can optionally be performed in order to aid in removal of any residual root canal filling materials from the tooth and oral cavity.

EXAMPLES

Example 1

The effectiveness of the compositions described herein for removing ZOE-containing temporary cements was tested using human dentin sample, i.e., extracted human teeth. Three dentin samples were first prepared by applying a clinically relevant film of ZOE cement to the samples and allowing the film to cure. Three different methods for removing the ZOE cement from the dentin samples were tested. In the first sample, a formulation containing 80% limonene, 10% isopentyl acetate, 6.9% isobutyl acetate, 3% propylene carbonate, and 0.1% quaternary ammonium salt was applied to the sample at a volume of 0.1 ml for 1 minute. To the second sample was applied Orange Solvent (DUX® Dental, Catalog Number 23031), a commercially available remover of ZOE cements, at a volume of 0.1 ml for 1 minute. Orange Solvent contains toxic ingredients, and therefore, can only be used for cleaning instruments and prosthesis located outside of the mouth. The third sample was cleaned by applying mechanical scraping with dental explorer for 1 minute.

Figure 1:
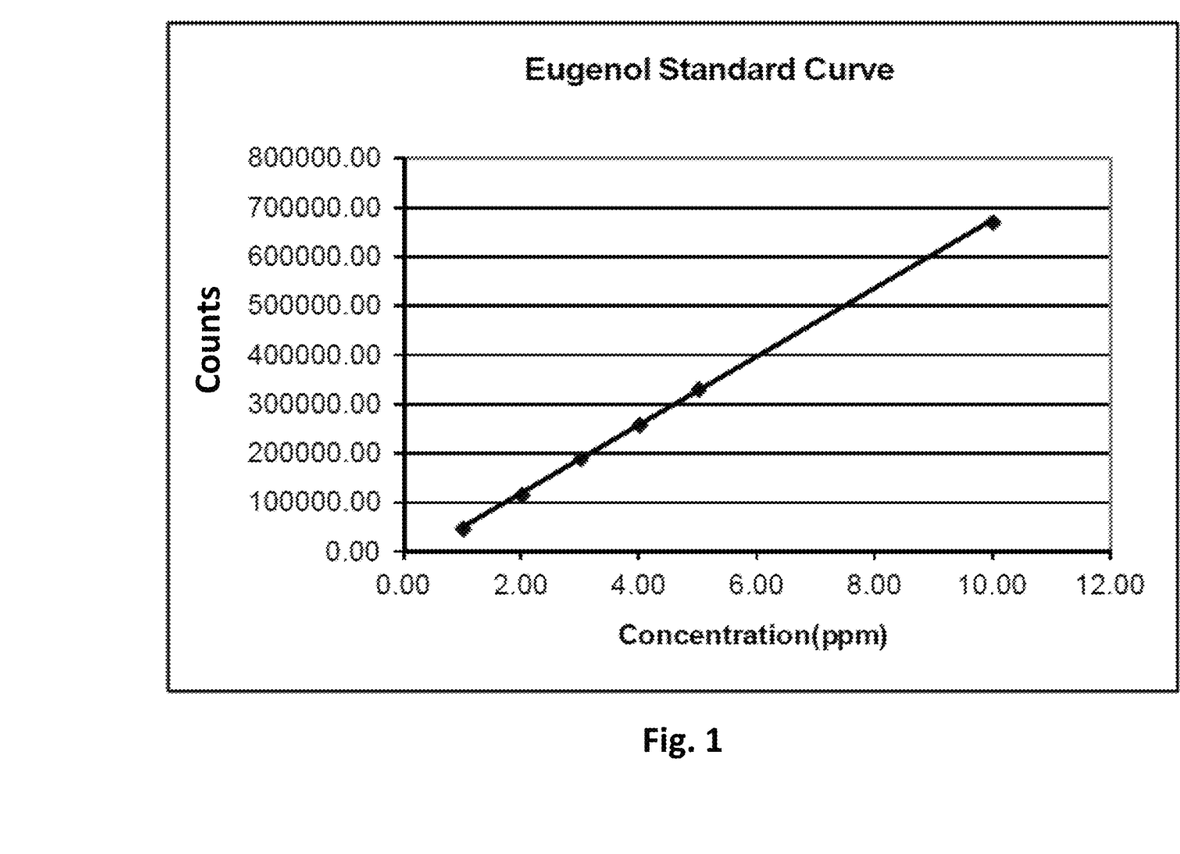
FIG. 1 demonstrates the removal of eugenol from human dentin samples.

After applying each removal method, the amount of residual eugenol attached to the dentin surface was determined by removing any residual eugenol with dichloromethane and analyzing by gas chromatography-mass spectrometry (GC-MS). The amount of residual eugenol in parts per million (ppm) was calculated using the slope of a calibration curve (FIG. 1) as determined by GC/MS analysis. The amount of eugenol remaining on each sample after attempted removal is summarized in Table 1 below.

TABLE 1

| ZOE Removal Method | Residual Eugenol (ppm) |
|---|---|
| Embodiment of Invention | 4.2 |
| Orange Solvent | 16.7 |
| Mechanical Scraping | 20.8 |

As demonstrated in the table above, the compositions described herein are more effective in removing eugenol from dentin samples then by either the currently available solvents (Orange Solvent) or by mechanical scraping. In addition, unlike Orange Solvent, the compositions described herein are safe for use inside the oral cavity and do not require special disposal procedures.

Example 2

Figure 2A:
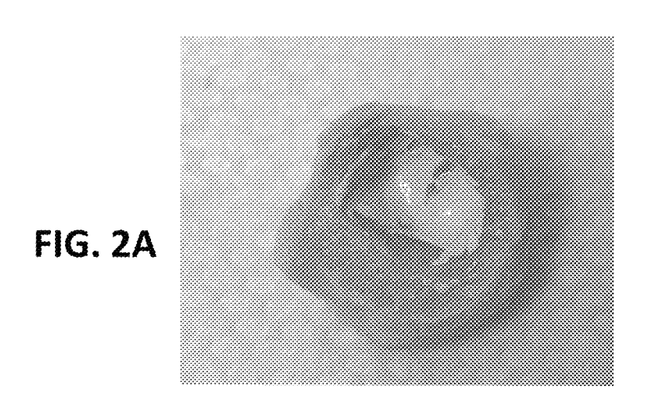
FIGS. 2A-2D demonstrate the removal of ZOE-containing cement from temporary crowns using one embodiment of a composition described herein.
Figure 2B:
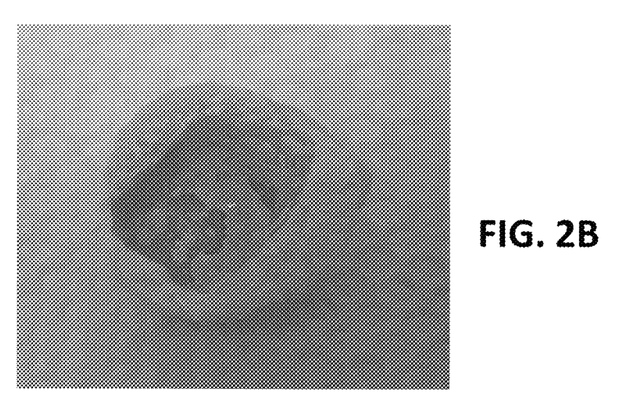
Figure 2C:
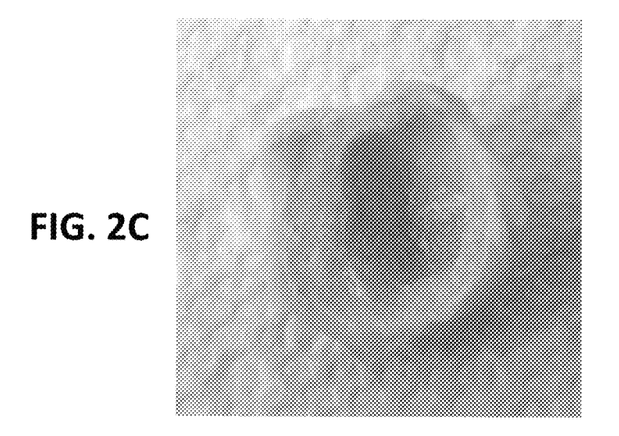
Figure 2D:
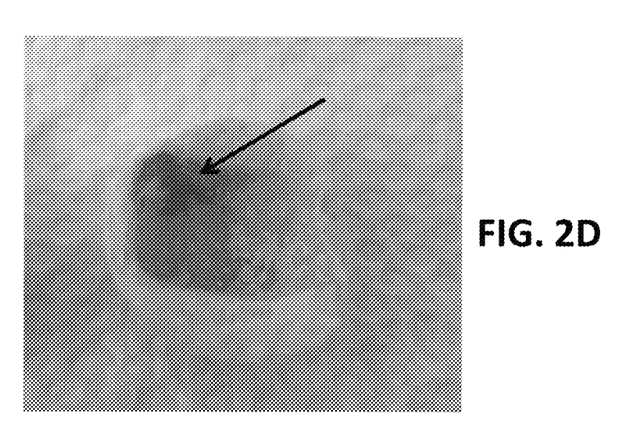

The effectiveness of the compositions described herein for removing ZOE-containing cement from temporary crowns is demonstrated in FIGS. 2A-2D. A set of temporary crowns was prepared by applying a generous amount of cement to a tooth. The crown was placed over the tooth and the cement allowed to cure. After curing, the crown was removed from the tooth leaving a film of residual temporary cement on the crown. FIGS. 2A and 2B contain images taken of the crowns before treatment with the following compositions. Two different compositions for removing the ZOE cement from the crowns were tested. In the first sample, the crown was submerged in 50 ml of a composition containing 70% limonene, 10% ethyl heptanoate, 10% isoamyl acetate, 6.9% propyl acetate, 3% propylene carbonate, and 0.1% benzalkonium chloride and ultrasonically treated for 10 minutes. The second sample was submerged in 50 ml of Temporary Cement Remover (Henry Schein® Dental, Catalog Number 100-5168), a commercially available remover of ZOE cements, and ultrasonically treated for 10 minutes. As FIGS. 2C-2D demonstrate, after chemical dissolution and ultrasonic treatment, near complete removal of the temporary cement was accomplished with the composition of the present invention (FIG. 2C). However, the crown treated with the commercially available Temporary Cement Remover contains a large amount of residual temporary cement as indicted by the arrow in FIG. 2D.

Example 3

Figure 3A:
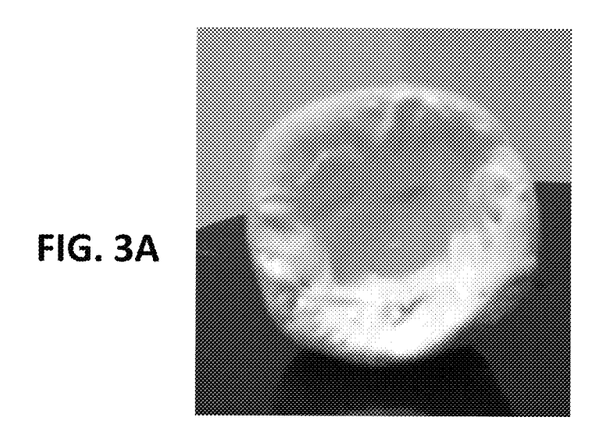
FIGS. 3A-3D demonstrate the removal of ZOE-containing cement from temporary crowns using another embodiment of a composition described herein.
Figure 3B:
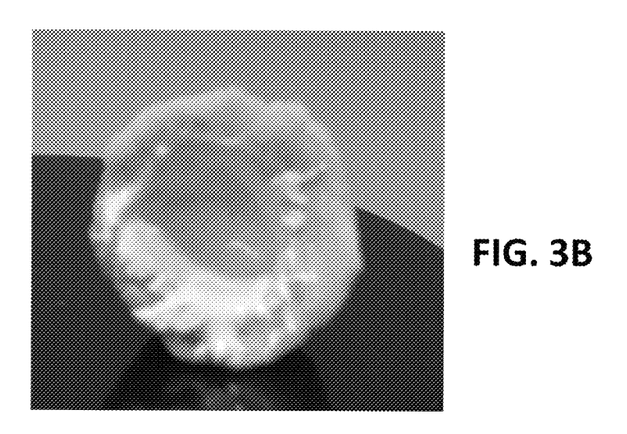
Figure 3C:
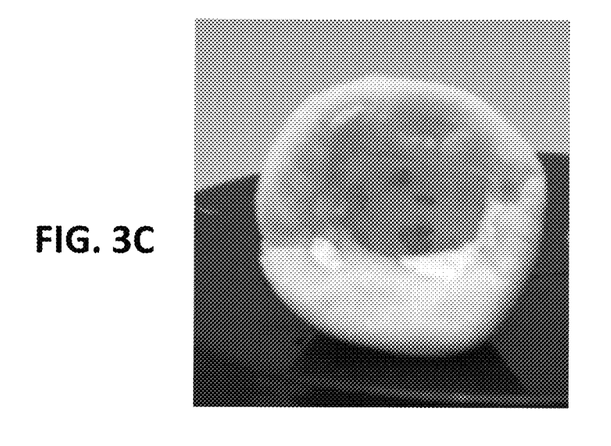
Figure 3D:
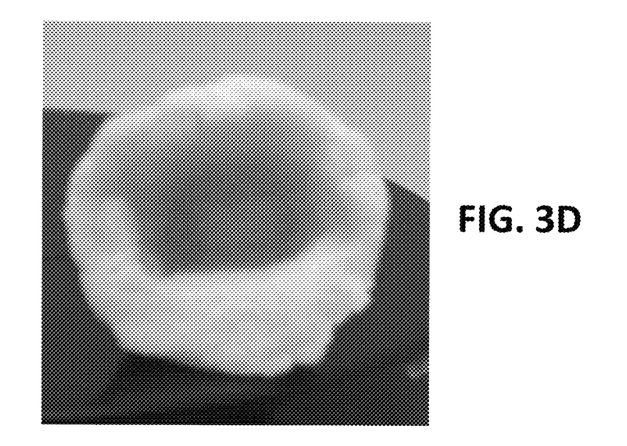

The effectiveness of the compositions described herein for removing ZOE-containing cement from temporary crowns is demonstrated in FIGS. 3A-3D. A set of temporary crowns was prepared by applying a generous amount of cement to a tooth. The crown was placed over the tooth and the cement allowed to cure. After curing, the crown was removed from the tooth leaving a film of residual temporary cement on the crown. FIGS. 3A and 3B contain images taken of the crowns before treatment with the following compositions. Two different compositions for removing the ZOE cement from the crowns were tested. In the first sample, the crown was submerged in 50 ml of a composition containing 80% limonene, 10% isopentyl acetate, 6.9% isobutyl acetate, 3% propylene carbonate, and 0.1% benzalkonium chloride and ultrasonically treated for 10 minutes. The second sample was submerged in 50 ml of Advanced Formula Temporary Cement Remover (Henry Schein® Dental, Catalog Number 924-1544), a commercially available remover of ZOE cements, and ultrasonically treated for 10 minutes. As FIGS. 3C-3D demonstrate, after chemical dissolution and ultrasonic treatment, near complete removal of the temporary cement was accomplished with the composition of the present invention (FIG. 3D). However, the crown treated with the commercially available Advanced Formula Temporary Cement Remover contains a large amount of residual temporary cement as can be seen in FIG. 3C.

Example 4

Applicants believe that the compositions described herein which contain a desensitizing agent increase adhesion of acrylate resin cements to collagen-containing surfaces by occluding the dentinal tubules of the collagen-containing surface, providing a smoother surface for resin cement bonding. In order to demonstrate that the compositions described herein occlude dentin tubules, teeth samples were treated according to the table below.

TABLE 2

| Embodiment of Invention | 8% limonene;<br>1% isopentyl acetate;<br>0.7% isobutyl acetate;<br>0.3% propylene carbonate;<br>0.1% benzalkonium chloride;<br>5% shellac;<br>84.89% ethanol; and<br>0.01% butylated hydroxytoluene |
|---|---|
| Negative Control | No Treatment |
| G5 All-Purpose Desensitizer (Clinician's Choice Catalog No. 226110) | 25-45% hydroxyethyl methacrylate and<br>1-5% glutaraldehyde |

Figure 4A:
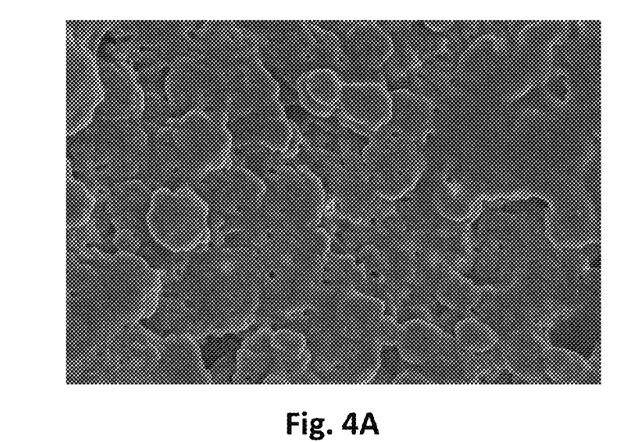
FIGS. 4A-4C demonstrate dentinal occlusion using one embodiment of a composition described herein.
Figure 4B:
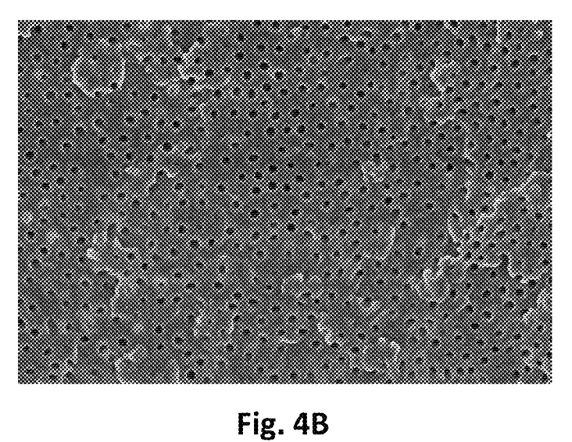
Figure 4C:
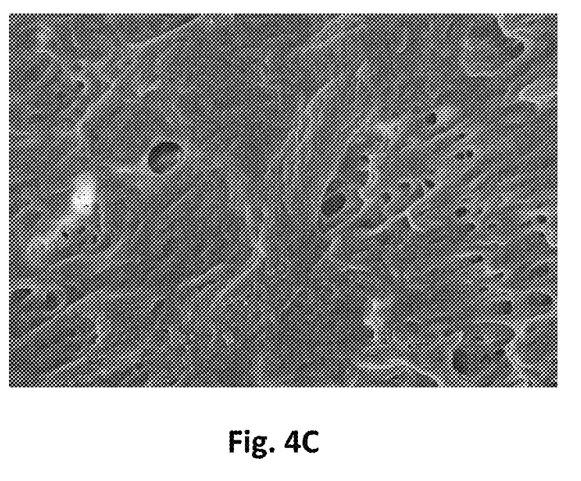

The samples were treated for 15 seconds with each of the compositions of Table 2 and then air dried with a blast of air. Scanning electron microscopy (SEM) images were taken of each sample to observe the occlusion of dentinal tubules (See FIGS. 4A-4C). FIG. 4A is a SEM image of the tooth treated with the composition of one embodiment containing 5% shellac. With this treatment, the dentinal tubules have been completely occluded. FIG. 4B is a SEM image of the negative control in which the dentinal tubules are clearly visible and open. FIG. 4C is a SEM image of the tooth treated with G5 All-Purpose Desensitizer in which a portion of the dentinal tubules are occluded but many tubules are still left open. These results indicate that the compositions and methods of the present invention containing shellac are significantly better than commercially available products at occluding dentinal tubules, and therefore, provide greater adhesion of acrylate resins cements to collagen containing surface.

Example 5

Figure 5A:
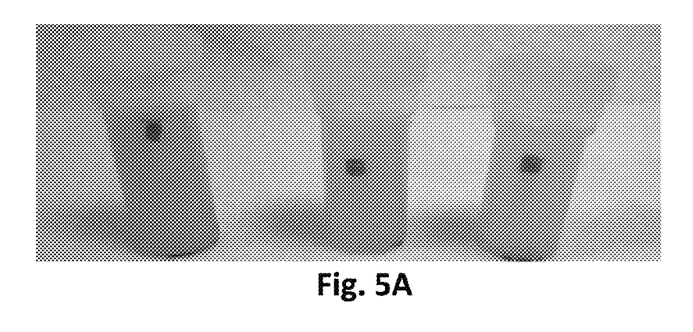
FIGS. 5A-5C demonstrate dissolution of a gutta-percha cone using one embodiment of a composition described herein.
Figure 5B:
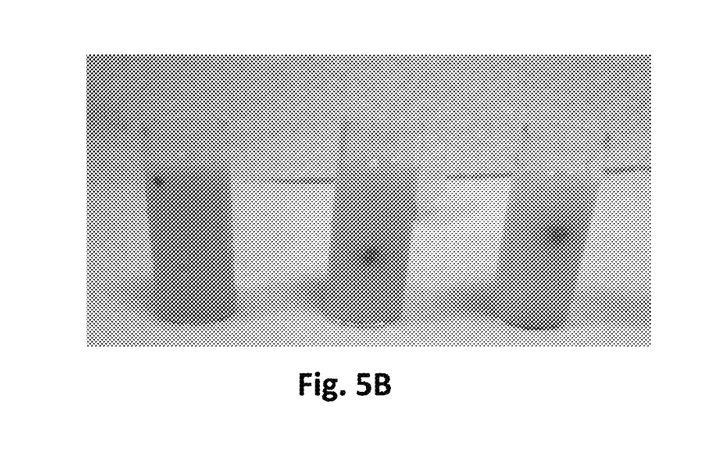
Figure 5C:
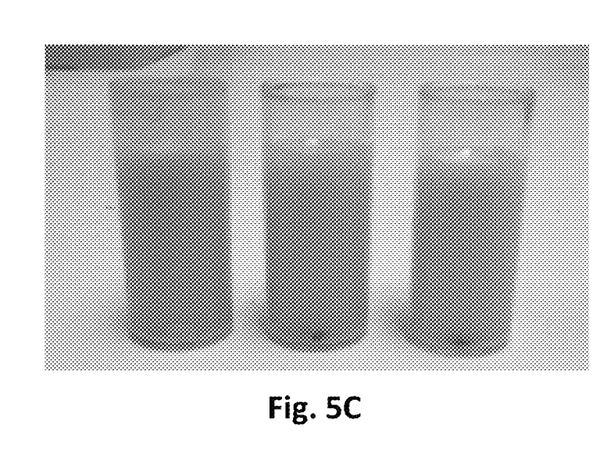

The compositions described herein were tested for their ability to dissolve root canal filling materials, particularly gutta-percha cones (See FIGS. 5A-5C). To perform this test, three different compositions were used: chloroform, Xylol (a xylene product manufactured by Sultan Healthcare No. 21401) and a composition of one embodiment of the invention containing 70% limonene, 15% propyl acetate, and 15% ethyl heptanoate. Images were taken of the gutta-percha cone at 3 minutes (FIG. 5A), 5 minutes (FIG. 5B), and 10 minutes (FIG. 5C) after immersion of the cone with each of the three compositions. For FIGS. 5A-5C, the sample treated with chloroform is on the left, the sample treated with Xylol is in the middle, and the sample treated with the composition of the invention is on the right. The results demonstrate that complete dissolution of the gutta-percha cone occurs by 10 minutes in all three samples.

Example 6

Figure 6A:
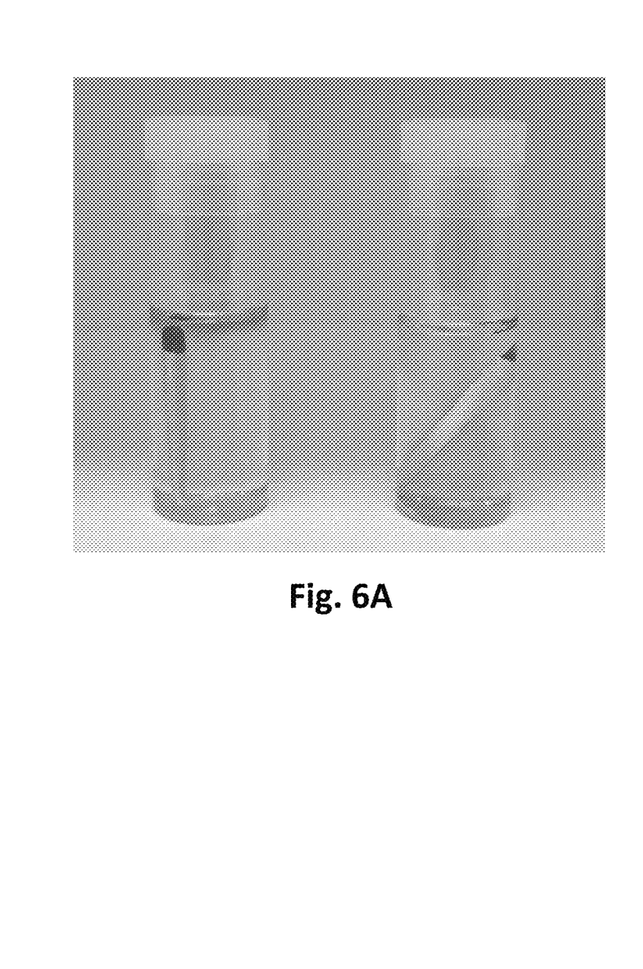
FIGS. 6A-6B demonstrate dissolution of a gutta-percha cone using another embodiment of a composition described herein.
Figure 6B:
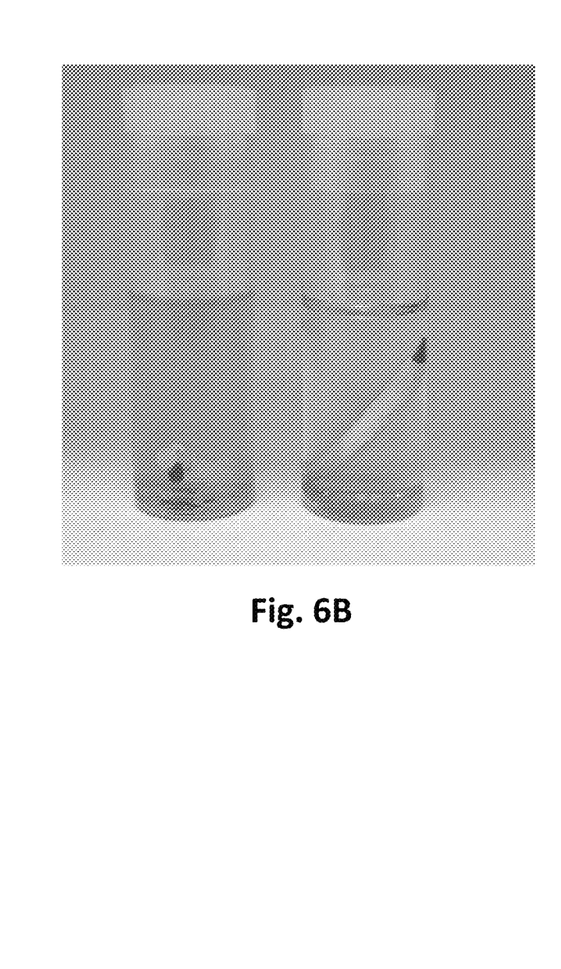

The compositions described herein were tested for their ability to dissolve root canal filling materials, particularly gutta-percha cones (See FIGS. 6A-6C). To perform this test, two different compositions were used: Xylol and a composition of one embodiment of the invention containing 80% limonene, 10% ethyl heptanoate, and 10% propyl acetate. Images were taken of the gutta-percha cone at 3 seconds (FIG. 6A) and at 60 seconds (FIG. 6B) after immersion of the cone with each of the compositions. For FIGS. 6A and 6B, the sample treated with Xylol is on the right and the sample treated with the composition of the invention is on the left. These results demonstrate that almost complete dissolution of the gutta-percha cone occurs within 60 seconds of treatment with the composition of the present invention, whereas there is no dissolution of the sample treated with Xylol at this time.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A removal composition, comprising at least one essential oil, at least one aliphatic ester, at least one cyclic ester selected from a group consisting of propylene carbonate and propiolactone in a concentration of 0.1% to 6% parts by weight of the total composition, and at least one quaternary ammonium salt,
    wherein the removal composition chemically removes a zinc-oxide eugenol-based product from a living or non-living object.

2. The composition of claim 1, wherein the at least one essential oil is selected from the group consisting of limonene, eucalyptol, and ethyl heptanoate; the at least one aliphatic ester is selected from the group consisting of isopentyl acetate, isoamyl acetate, isobutyl acetate, benzyl acetate, methyl salicylate, ethyl acetate, and propyl acetate; and the at least one quaternary ammonium salt is selected from the group consisting of tetra-n-butylammonium bromide, cetrimonium bromide, and benzalkonium chloride.

3. The composition of claim 1, wherein the concentration of the at least one essential oil is 50% to 99% parts by weight of the total composition; the concentration of the at least one aliphatic ester is 5% to 40% parts by weight of the total composition; and the concentration of the at least one quaternary ammonium salt is 0.01% to 4% parts by weight of the total composition.

4. The composition of claim 1 comprising limonene at a concentration of 80% parts by weight of the total composition; isopentyl acetate at a concentration of 10% parts by weight of the total composition; isobutyl acetate at a concentration of 6.9% parts by weight of the total composition; propylene carbonate at a concentration of 3% parts by weight of the total composition; and benzalkonium chloride at a concentration of 0.1% parts by weight of the total composition.

5. The composition of claim 1, wherein the composition is orally-acceptable.

6. A method for removing a zinc-oxide eugenol-based product from a living or non-living object, comprising:
  a. chemically dissolving the zinc-oxide eugenol-based product by immersing or coating the object in a composition comprising at least one essential oil, at least one aliphatic ester, at least one cyclic ester selected from a group consisting of propylene carbonate and propiolactone in concentration of 0.1% to 6% parts by weight of the total composition, and at least one quarternary ammonium salt; and
  b. optionally, mechanically treating the object.

7. The method of claim 6, wherein the step of mechanically treating the living object comprises scraping, rubbing, brushing, or combinations thereof; and the step of mechanically treating the non-living object comprises subjecting to mechanical vibrations, subjecting to ultrasound, or combinations thereof.

8. The method of claim 6, wherein the composition comprises limonene at a concentration of 80% parts by weight of the total composition; isopentyl acetate at a concentration of 10% parts by weight of the total composition; isobutyl acetate at a concentration of 6.9% parts by weight of the total composition; propylene carbonate at a concentration of 3% parts by weight of the total composition; and benzalkonium chloride at a concentration of 0.1% parts by weight of the total composition.

* * * * *